US009681659B2

(12) United States Patent
Taranta et al.

(10) Patent No.: US 9,681,659 B2
(45) Date of Patent: *Jun. 20, 2017

(54) AGROCHEMICAL FORMULATION COMPRISING ENCAPSULATED PESTICIDE

(75) Inventors: Claude Taranta, Stutensee (DE); Thomas Bork, Westhofen (DE); Tina Schroeder-Grimonpont, Rheinzabern (DE); Britta Katz, Dannstadt-Schauerheim (DE); Tatjana Sikuljak, Mannheim (DE); Simon Nord, Karlsruhe (DE); Juergen Distler, Freimersheim (DE); Richard A. Warriner, Wake Forest, NC (US); Daniel Bihlmeyer, Apex, NC (US); James Thomas Wofford, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 42 days.

This patent is subject to a terminal disclaimer.

(21) Appl. No.: 13/980,936

(22) PCT Filed: Jan. 23, 2012

(86) PCT No.: PCT/EP2012/050925
§ 371 (c)(1),
(2), (4) Date: Jul. 22, 2013

(87) PCT Pub. No.: WO2012/101070
PCT Pub. Date: Aug. 2, 2012

(65) Prior Publication Data
US 2013/0295152 A1 Nov. 7, 2013

Related U.S. Application Data

(60) Provisional application No. 61/435,380, filed on Jan. 24, 2011.

(30) Foreign Application Priority Data

Feb. 21, 2011 (EP) .................. 11155174

(51) Int. Cl.
*A01N 25/04* (2006.01)
*A01N 25/22* (2006.01)
*A01N 25/28* (2006.01)
*A01N 53/00* (2006.01)

(52) U.S. Cl.
CPC ............ *A01N 25/04* (2013.01); *A01N 25/28* (2013.01); *A01N 53/00* (2013.01)

(58) Field of Classification Search
CPC ........ A01N 25/04; A01N 25/22; A01N 25/28; A01N 25/30; A01N 53/00
See application file for complete search history.

(56) References Cited

U.S. PATENT DOCUMENTS

| 8,034,887 | B2 | 10/2011 | Jung et al. |
|---|---|---|---|
| 8,535,558 | B2 | 9/2013 | Jung et al. |
| 9,241,912 | B2* | 1/2016 | Taranta ............... A61K 9/5031 |
| 2004/0197357 | A1 | 10/2004 | Heming et al. |
| 2008/0166555 | A1 | 7/2008 | Lang-Wittkowski et al. |
| 2008/0318048 | A1 | 12/2008 | Amrhein et al. |
| 2009/0105073 | A1* | 4/2009 | Taranta ................. A01N 25/02 |
| | | | 504/100 |
| 2009/0256107 | A1 | 10/2009 | Hentze et al. |
| 2010/0036020 | A1 | 2/2010 | Zhao et al. |
| 2010/0068525 | A1 | 3/2010 | Jung et al. |
| 2010/0168275 | A1 | 7/2010 | Zhao et al. |
| 2010/0323892 | A1 | 12/2010 | Levy et al. |
| 2010/0327216 | A1 | 12/2010 | Jung et al. |
| 2011/0003152 | A1 | 1/2011 | Grey |

(Continued)

FOREIGN PATENT DOCUMENTS

| DE | 102005 002411 | 7/2006 |
|---|---|---|
| WO | WO 02/100525 | 12/2002 |
| WO | WO 2004/017734 | 3/2004 |

(Continued)

OTHER PUBLICATIONS

International Preliminary Report on Patentability dated Jul. 30, 2013, prepared in International Application No. PCT/EP2012/050925.
International Search Report dated Jun. 20, 2012, prepared in International Application No. PCT/EP2012/050925.

*Primary Examiner* — John Pak
*Assistant Examiner* — Nathan W Schlientz
(74) *Attorney, Agent, or Firm* — Brinks Gilson & Lione

(57) ABSTRACT

The present invention relates to a aqueous composition containing a suspended pesticide A, and microcapsules comprising a shell and a core, wherein the core contains a pesticide B and an aprotic, polar solvent B, and the shell contains poly(meth)acrylate, which comprises $C_1$-$C_{24}$ alkyl esters of acrylic and/or methacrylic acid, acrylic acid, methacrylic acid, and/or maleic acid in polymerized form. The invention further relates to a method for preparing said composition comprising the mixing of the pesticide A, water and the microcapsules, to said microcapsule, wherein the core contains the pesticide B and a solvent A, wherein the weight ratio of the pesticide B to the sum of all solvents in the core is from 1:1 to 1:10, and wherein the microcapsule contains up to 7 wt % poly(meth)acrylate, based on the total amount of all pesticides in the core, all solvents in the core, and the poly(meth)acrylate.

13 Claims, No Drawings

(56) References Cited

U.S. PATENT DOCUMENTS

2012/0076843 A1   3/2012   Jung et al.

FOREIGN PATENT DOCUMENTS

| WO | WO 2006/092439 | 9/2006 |
| WO | WO2008/006762 | 1/2008 |
| WO | WO 2008/058868 | 5/2008 |
| WO | WO 2008/064999 | 6/2008 |
| WO | WO 2008/151941 | 12/2008 |
| WO | WO 2010/105971 | 9/2010 |
| WO | WO 2010/145993 | 12/2010 |
| WO | WO 2011/004006 | 1/2011 |
| WO | WO 2012/095436 | 7/2012 |

* cited by examiner

AGROCHEMICAL FORMULATION COMPRISING ENCAPSULATED PESTICIDE This application is a National Stage application of International Application No. PCT/EP2012/050925, filed Jan. 23, 2012, which claims the benefit of U.S. Provisional Application No. 61/435,380, filed Jan. 24, 2011, the entire contents of which are hereby incorporated herein by reference. This application also claims priority under 35 U.S.C. §119 to European Patent Application No. 11155174.3, filed Feb. 21, 2011, the entire contents of which is hereby incorporated herein by reference.

The present invention relates to a aqueous composition containing a suspended pesticide A, and microcapsules comprising a shell and a core, wherein the core contains a pesticide B and an aprotic, polar solvent B, and the shell contains poly(meth)acrylate, which comprises $C_1$-$C_{24}$ alkyl esters of acrylic and/or methacrylic acid, acrylic acid, methacrylic acid, and/or maleic acid in polymerized form. The invention further relates to a method for preparing said composition comprising the mixing of the pesticide A, water and the microcapsules, to said microcapsule, wherein the core contains the pesticide B and a solvent A and an aprotic, polar solvent B, wherein the weight ratio of the pesticide B to the sum of all solvents in the core is from 1:1 to 1:10, and wherein the microcapsule contains up to 7 wt % poly(meth)acrylate, based on the total amount of all pesticides in the core, all solvents in the core, and the poly(meth)acrylate; to a method for preparing said microcapsules comprising the step of heating an oil-in-water emulsion, which contains a radical initiator, the solvent A and the pesticide B, and a monomer selected from $C_1$-$C_{24}$ alkyl esters of acrylic and/or methacrylic acid, acrylic acid, methacrylic acid, and/or maleic acid; and finally to a method for controlling phytopathogenic fungi and/or undesired plant growth and/or undesired attack by insects or mites and/or for regulating the growth of plants, where the said microcapsules or said aqueous composition is allowed to act on the particular pests, their habitat or the plants to be protected from the particular pest, the soil and/or on undesired plants and/or the useful plants and/or their habitat. Combinations of preferred embodiments with other preferred embodiments are within the scope of the present invention.

Microcapsules comprising a poly(meth)acrylate shell and a core, which contains a pesticide are known. The state of the art has various disadvantages: high tendency of crystallization of the active ingredients; it low stability of the formulation within broad range of temperatures; low compatibility with other pesticides; high wind drift; active ingredients are decomposed by UV-light; low rainfastness. Object of the present invention was to overcome such disadvantages.

The object was solved by an aqueous composition containing a suspended pesticide A, and microcapsules comprising a shell and a core, wherein the core contains a pesticide B and an aprotic, polar solvent B, and the shell contains poly(meth)acrylate, which comprises $C_1$-$C_{24}$ alkyl esters of acrylic and/or methacrylic acid, acrylic acid, methacrylic acid, and/or maleic acid in polymerized form.

The aqueous composition may contain from 5 to 80 wt % water, preferably from 10 to 70 wt %, and in particular from 20 to 55 wt %.

The aqueous composition contains usually from 5 to 80 wt % of the microcapsules, preferably from 10 to 60 wt %. The aqueous composition contains usually at least 2 wt % encapsulated pesticide, preferably at least 5 wt % and in particular at least 8 wt %.

The term pesticide refers to at least one active substance selected from the group of the fungicides, insecticides, nematicides, herbicides, safeners and/or growth regulators. Preferred pesticides are fungicides, insecticides, herbicides and growth regulators. Especially preferred pesticides are insecticides. Mixtures of pesticides of two or more of the abovementioned classes may also be used. The skilled worker is familiar with such pesticides, which can be found, for example, in the Pesticide Manual, 15th Ed. (2009), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

Pesticide A is a pesticide, which is suspended in the aqueous composition. The particle size of the suspended pesticide particles is as usual, for example from 0.9 to 50 µm, preferably from 1 to 20 µm.

The pesticide A has preferably a solubility in water of less than 10 g/l at 20° C. More preferably, it has solubility of less than 1.0 g/l, in particular of less than 0.2 g/l. For example, the solubilities in water are: pyraclostrobin 1.9 mg/l, prochloraz 34 mg/L, metrafenon 0.5 mg/l, alphacypermethrin 0.01 mg/l.

The pesticide A has usually a melting point of at least 30° C., preferably at least 40° C., and in particular at least 45° C. For example the melting points are: pyraclostrobin 64° C., prochloraz 47° C., metrafenon 100° C., alphacypermethrin 79° C.

The pesticide A comprises preferably an insecticide, in particular alphacypermethrin.

Pesticide B is a pesticide, which is contained in the core of the microcapsules. The pesticide B may be present in the core in dissolved form, as suspension, emulsion or suspoemulsion. Preferably, the pesticide B is present in dissolved form.

The pesticide B has usually a solubility in a mixture of aromatic hydrocarbons with a distillation range of 235-290° C. (e.g. Solvesso® 200 ND) and 2-heptanon (1:1 wt %) of at least 10 wt %, preferably at least 20 wt %, and in particular at least 30 wt %, at 20° C.

The pesticide B has preferably a solubility in water of less than 10 g/l at 20° C. More preferably, it has solubility of less than 1.0 g/l, in particular of less than 0.2 g/l.

The pesticide B has usually a melting point of at least 30° C., preferably at least 40° C., and in particular at least 45° C.

Pesticide A and pesticide B might be identical or different, preferably they are identical. Preferably, pesticide A and B are both either insecticides, herbicides or fungicides (in particular insecticides).

The core may contain a water-immiscible solvent A. Suitable examples for water-immiscible solvent A are
  a hydrocarbon solvent such a an aliphatic, cyclic and aromatic hydrocarbons (e. g. toluene, xylene, paraffin, tetrahydronaphthalene, alkylated naphthalenes or their derivatives, mineral oil fractions of medium to high boiling point (such as kerosene, diesel oil, coal tar oils));
  a vegetable oil such as corn oil, rapeseed oil;
  a fatty acid ester such as $C_1$-$C_{10}$-alkylester of a $C_{10}$-$C_{22}$-fatty acid; or
  methyl- or ethyl esters of vegetable oils such as rapeseed oil methyl ester or corn oil methyl ester.

Mixtures of aforementioned solvents are also possible. Preferred solvents A are hydrocarbons, in particular aromatic hydrocarbons.

Preferably, solvent A has a solubility in water of up to 50 g/l at 20° C., more preferably of up to 5 g/l and in particular of up to 0.5 g/l.

Usually, solvent A has a boiling point above 100° C., preferably above 150° C., and in particular above 180° C.

The core may contain an aprotic, polar solvent B. The aprotic, polar solvent B has usually a solubility in water from 0.5 to 50 g/l at 20° C. Preferably, solvent B has a solubility in water from 0.5 to 20.0 g/l, in particular from 0.5 to 10.0 g/L. Mixtures of different kinds of solvent B are also possible. Typically, solvent B is free of carbon-carbon double and/or triple bonds to avoid side reactions.

Preferably, solvent B is a ketone, such as an aliphatic or aromatic ketone. Suitable examples are acetophenone, 2-heptanone, or cyclohexanone. More preferably, solvent B is a ketone, which has a solubility in water from 0.5 to 20 g/l at 20° C. In particular, solvent B is 2-heptanone.

For example, some solubility values are listed (all data at 20° C.): acetophenon 5.5 g/l, 2-Heptanon 4.3 g/l, 3-heptanone (2.6 g/l), 2-hexanone (14 g/l), 5-methyl-2-hexanone (5.4 g/l), 5-methyl-3-heptanone (3.0 g/l), 3-methyl-2-hexanone (4.1 g/l), 4-methyl-2-hexanone (4.3 g/l), 2-methyl-3-hexanone (6.3 g/l), 4-methyl-3-hexanone (5.2 g/l), 5-methyl-3-hexanone (5.2 g/l), 3-ethyl-2-pentanone (4.6 g/l), 3,3-dimethyl-2-pentanone (7.3 g/l), 3,4-dimethyl-2-pentanone (6.7 g/l), 4,4-dimethyl-2-pentanone (10.4 g/l), 2,2-dimethyl-3-pentanone (10.4 g/l), 2,4-dimethyl-3-pentanone (5.7 g/l), 2-octanone (0.9 g/l), 2,5-dimethyl-3-hexanone (2.6 g/l), 2,2-dimethyl-3-hexanone (2.8 g/l), 3,3-dimethyl-2-hexanone (2.7 g/l), 3,4-dimethyl-2-hexanone (1.4 g/l), 4,4-dimethyl-3-hexanone (2.5 g/l), 3-ethyl-4-methyl-2-pentanone (1.7 g/l), 2-methyl-3-heptanone (1.4 g/l), 2-methyl-4-heptanone (1.7 g/l), 3-methyl-2-heptanone (0.9 g/l), 3-methyl-4-heptanone (1.9 g/l), 5-methyl-3-heptanone (1.1 g/l), 6-methyl-2-heptanone (0.8 g/l), 6-methyl-3-heptanone (0.9 g/l), 3-octanone (0.8 g/l), 4-octanone (1.0 g/l), 2,2,4-trimethyl-3-pentanone (5.5 g/l), 3-ethyl-3-methyl-2-pentanone (1.8 g/l), 5-methyl-2-heptanone (1.0 g/l), isoporone (15 g/l).

The core may contain either solvent A or solvent B, or it may contain both solvent A and solvent B. Preferably, the core contains solvent A and optionally solvent B.

In particular, the core contains solvent A and solvent B. In this case is the weight ratio of solvent A to solvent B is usually in the range from 5:95 to 95:5, preferably from 10:1 to 1:5, more preferably from 5:1 to 1:2, and in particular from 3:1 to 1:1.

The core may contain further solvents in addition to solvent A and solvent B. Usually, the core comprises less than 40 wt %, preferably less than 20 wt %, and in particular less than 5 wt % of further solvents, based on the total weight of all solvents in the core.

The weight ratio of the sum of all pesticides in the core (e.g. pesticide B) to the sum of all solvents in the core (e.g. solvent A and solvent B) is typically from 5:1 to 1:20, preferably from 1:1 to 1:10, more preferably from 1:1.2 to 1:5, and in particular from 1:1.5 to 1:3.

The core contains at least 5 wt %, preferably at least 15 wt % and in particular at least 25 wt % of pesticide (e.g. pesticide B), based on the total amount of the core materials. The core may contain up to 70 wt %, preferably up to 50 wt % of pesticide. The amount of core materials is typically summed up from the amounts of all pesticides and solvents in the core.

The core contains at least 10 wt %, preferably at least 20 wt % and in particular at least 35 wt % of solvent A, based on the total amount of the core materials. The core may contain up to 90 wt %, preferably up to 70 wt % of solvent A.

The core contains at least 5 wt %, preferably at least 10 wt % and in particular at least 18 wt % of solvent B, based on the total amount of the core materials. The core may contain up to 80 wt %, preferably up to 65 wt % of solvent B.

The core may optionally contain auxiliaries, such as those mentioned below. Preferably, the core contains at least one adjuvant (for example organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®).

Preferably, the microcapsule contains up to 7 wt % poly(meth)acrylate, based on the total amount of all pesticides in the core (e.g. pesticide B), all solvents in the core (e.g. solvent A and B) and poly(meth)acrylate. Especially preferred is a microcapsule, which contains up to 6.5 wt %, especially 6.0 wt % and in particular 5.5 wt %. The microcapsules contain usually at least 0.5 wt %, preferably at least 1.5 wt %, and in particular 2.5 wt % poly(meth)acrylate.

The amount of poly(meth)acrylate is calculated by adding up the amount of monomers, which were used to synthesize the shell (such as the $C_1$-$C_{24}$ alkyl esters of acrylic and methacrylic acid, acrylic acid, methacrylic acid, and maleic acid).

The average particle size of the capsules (z-average by means of light scattering; preferably a $D_{4,3}$ average) is 0.5 to 50 μm, preferably 0.5 to 20 μm, more preferably 1 to 10 μm, and especially 1 to 8 μm.

The shell contains poly(meth)acrylate, which comprises $C_1$-$C_{24}$ alkyl esters of acrylic and/or methacrylic acid, acrylic acid, methacrylic acid, and/or maleic acid in polymerized form.

Typically, the poly(meth)acrylate contains in polymerized form
30 to 100% by weight of one or more $C_1$-$C_{24}$-alkyl esters of acrylic acid and/or methacrylic acid, acrylic acid, methacrylic acid and/or maleic acid (monomers I),
0 to 70% by weight of one or more difunctional and/or polyfunctional monomers (monomers II), and
0 to 40% by weight of one or more other monomers (monomer III),
in each case based on the total weight of the monomers.

Preferably, the poly(meth)acrylate contains in polymerized form
30 to 90% by weight of one or more $C_1$-$C_{24}$-alkyl esters of acrylic acid and/or methacrylic acid, acrylic acid, methacrylic acid and/or maleic acid (monomers I),
10 to 70% by weight of one or more difunctional and/or polyfunctional monomers (monomers II), and
0 to 40% by weight of one or more other monomers (monomer III),
in each case based on the total weight of the monomers.

The polymerization of said monomers usually results in a poly(meth)acrylate. Poly(meth)acrylate is a known encapsulation material, for example from WO 2008/071649, EP 0 457154 or DE 10 2007 055 813.

The poly(meth)acrylate of the capsule wall comprise generally at least 30%, in a preferred form at least 40%, in a particularly preferred form at least 50%, more particularly at least 55%, with very particular preference at least 70%, and also up to 100%, preferably not more than 90%, more particularly not more than 85%, and, with very particular preference, not more than 80%, by weight, of at least one monomer from the group comprising $C_1$-$C_{24}$ alkyl esters of acrylic and/or methacrylic acid, acrylic acid, methacrylic acid, and maleic acid (monomers I), in copolymerized form, based on the total weight of the monomers.

Furthermore the poly(meth)acrylate of the capsule wall comprises preferably at least 10%, preferably at least 15%, preferentially at least 20%, and also, in general, not more than 70%, preferably not more than 60%, and with particular preference not more than 50%, by weight, of one or more difunctional or polyfunctional monomers (monomers II), in copolymerized form, based on the total weight of the monomers. In another preferred embodiment, the poly(meth) acrylate of the capsule wall comprises preferably at least 10%, preferably at least 15%, and also, in general, not more than 50%, preferably not more than 40% by weight, of one or more polyfunctional monomers (monomers II), in copolymerized form, based on the total weight of the monomers.

Additionally, the poly(meth)acrylate may comprise up to 40%, preferably up to 30%, more particularly up to 20%, by weight, of other monomers III, in copolymerized form. The capsule wall is preferably synthesized only from monomers of groups I and II.

Suitable monomers I are $C_1$-$C_{24}$ alkyl esters of acrylic and/or methacrylic acid and also the unsaturated $C_3$ and $C_4$ carboxylic acids such as acrylic acid, methacrylic acid, and also maleic acid. Suitable monomers I are isopropyl, isobutyl, sec-butyl, and tert-butyl acrylates and the corresponding methacrylates, and also, with particular preference, methyl, ethyl, n-propyl, and n-butyl acrylates and the corresponding methacrylates. In general the methacrylates and methacrylic acid are preferred.

According to one preferred embodiment the microcapsule walls comprise 10% to 60% by weight of maleic acid, methacrylic acid and/or acrylic acid, more particularly methacrylic acid, based on the total amount of the monomers I, in copolymerized form.

Suitable monomers II are difunctional and/or polyfunctional monomers. By difunctional or by polyfunctional monomers are meant compounds which have at least two nonconjugated ethylenic double bonds. Contemplated primarily are divinyl monomers and polyvinyl monomers. They bring about crosslinking of the capsule wall during the polymerization. In another preferred embodiment, monomer II comprises one or more difunctional and polyfunctional monomers.

Suitable divinyl monomers are divinylbenzene and divinylcyclohexane. Preferred divinyl monomers are the diesters of diols with acrylic acid or methacrylic acid, and also the diallyl and divinyl ethers of these diols. Mention may be made, by way of example, of ethanediol diacrylate, ethylene glycol dimethacrylate, 1,3-butylene glycol dimethacrylate, methallylmethacrylamide, allyl acrylate, and allyl methacrylate. Particular preference is given to propanediol, 1,4-butanediol, pentanediol, and hexanediol diacrylates and the corresponding methacrylates.

Preferred polyvinyl monomers are the polyesters of polyols with acrylic acid and/or methacrylic acid, and also the polyallyl and polyvinyl ethers of these polyols, trivinylbenzene and trivinylcyclohexane. Particular preference is given to trimethylolpropane triacrylate and trimethacrylate, pentaerythritol triallyl ether, pentaerythritol tetraallyl ether, pentaerythritol triacrylate, and pentaerythritol tetraacrylate, and also their technical mixtures.

Monomers III contemplated are other monomers, different than the monomers I and II, such as vinyl acetate, vinyl propionate, vinylpyridine, and styrene or α-methylstyrene. Particular preference is given to itaconic acid, vinylphosphonic acid, maleic anhydride, 2-hydroxyethyl acrylate and methacrylate, acrylamido-2-methylpropanesulfonic acid, methacrylonitrile, acrylonitrile, methacrylamide, N-vinylpyrrolidone, N-methylolacrylamide, N-methylolmethacrylamide, dimethylaminoethyl methacrylate, and diethylaminoethyl methacrylate.

The protective colloid is generally incorporated into or on the capsule wall and is therefore likewise a constituent of the capsule wall. Generally speaking, the surface of the polymer has the protective colloid. Thus it is possible for there to be up to 10% by weight, based on the total weight of the microcapsules, of protective colloid.

The present invention further relates to a method for preparing the composition according to the invention, comprising the mixing of the pesticide A, water and the microcapsules. This may be done for example at room temperature. For mixing standard industrial mixing equipment may be used. Preferably, an aqueous suspension of pesticide A and an aqueous suspension of microcapsules, which contain the pesticide B, are mixed. Pesticide A and pesticide B are preferably identical.

In general, microcapsules may be prepared comprising the step of heating an oil-in-water emulsion, which contains a radical initiator, the pesticide B, and a monomer selected from $C_1$-$C_{24}$ alkyl esters of acrylic and/or methacrylic acid, acrylic acid, methacrylic acid, and/or maleic acid. The preparation process of the microcapsules is what is called an in situ polymerization. The principle of microcapsule formation is based on the preparation of a stable oil-in-water emulsion from the monomers, a free-radical initiator, the protective colloid, and the pheromone to be encapsulated. Subsequently the polymerization of the monomers is triggered by heating and is controlled, if appropriate, by further increase in temperature, the resulting polymers forming the capsule wall which encloses the pheromone. This general principle is described, for example, in DE A 101 39 171.

The aqueous compositions according to the invention may also comprise auxiliaries which are customary in agrochemical formulations. The auxiliaries used depend on the particular application form and active substance, respectively. Examples for suitable auxiliaries are dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable surface-active substances (adjuvants, wetters, stickers, dispersants or emulsifiers) are the alkali metal, alkaline earth metal and ammonium salts of aromatic sulfonic acids, for example of lingo- (Borresperse® types, Borregaard, Norway), phenol-, naphthalene- (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone, and their copolymers.

Surfactants which are particularly suitable are anionic, cationic, nonionic and amphoteric surfactants, block polymers and polyelectrolytes. Suitable anionic surfactants are alkali, alkaline earth or ammonium salts of sulfonates, sulfates, phosphates or carboxylates. Examples of sulfonates are alkylarylsulfonates, diphenylsulfonates, alpha-olefin sulfonates, sulfonates of fatty acids and oils, sulfonates of ethoxylated alkylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds such as alcohols, alkylphenols, amines (e.g. tallow amine), amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide or of the A-B-C type comprising alkanol, polyethylene oxide and polypropylene oxide. Suitable polyelectrolytes are polyacids or polybases. Examples of polyacids are alkali salts of polyacrylic acid. Examples of polybases are polyvinylamines or polyethyleneamines. The composition according to the invention may comprise at least 1 wt %, preferably at least 5 wt %, of a nonionic surfactant (e.g. an alkoxylate).

Examples for thickeners (i. e. compounds that impart a modified flowability to compositions, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidons, polyvinylacetates, polyvinyl alcohols and cellulose ethers (Tylose®, Shin-Etsu, Japan).

The present invention further relates to a microcapsule as defined above, wherein the core contains the pesticide B, the solvent A and the aprotic, polar solvent B, and the weight ratio of all pesticide B (in case more than one pesticide is present in the core, then of the sum of all pesticides in the core are applied) to the sum of all solvents in the core is from 1:1 to 1:10, and wherein the microcapsule contains up to 7 wt % poly(meth)acrylate, based on the total amount of pesticide, solvent and poly(meth)acrylate.

For example, the microcapsules comprise a shell and a core, wherein the core contains the pesticide B, the solvent A and the aprotic, polar solvent B, the shell contains poly(meth)acrylate, which comprises $C_1$-$C_{24}$ alkyl esters of acrylic and/or methacrylic acid, acrylic acid, methacrylic acid, and/or maleic acid in polymerized form, the weight ratio of the pesticide B to the sum of all solvents in the core is from 1:1 to 1:10, and the microcapsule contains up to 7 wt % poly(meth)acrylate, based on the total amount of all pesticides in the core, all solvents in the core, and the poly(meth)acrylate.

Further preferred embodiments of the microcapsules according to the invention are described above.

The present invention further relates to a method for preparing the microcapsules according to the invention, comprising the step of heating an oil-in-water emulsion, which contains a radical initiator, the solvent A, the aprotic, polar solvent B and the pesticide B, and a monomer selected from $C_1$-$C_{24}$ alkyl esters of acrylic and/or methacrylic acid, acrylic acid, methacrylic acid, and/or maleic acid. The preparation process of the microcapsules is what is called an in situ polymerization. The principle of microcapsule formation is based on the preparation of a stable oil-in-water emulsion from the monomers, a free-radical initiator, the protective colloid, the solvents, and the pesticide to be encapsulated. Subsequently the polymerization of the monomers is triggered by heating and is controlled, if appropriate, by further increase in temperature, the resulting polymers forming the capsule wall which encloses the pheromone. This general principle is described, for example, in DE A 101 39 171.

The present invention further relates to a method for controlling phytopathogenic fungi and/or undesired plant growth and/or undesired attack by insects or mites and/or for regulating the growth of plants, where the microcapsules or the aqueous composition according to the invention is allowed to act on the particular pests, their habitat or the plants to be protected from the particular pest, the soil and/or on undesired plants and/or the useful plants and/or their habitat.

Various plants my be treated, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants. Preferred plants are soybean, cotton, corn, alfalfa, wheat, and vegetables.

In the sense of the present invention, "insects or mites" are preferably selected from arthropods and nematodes, more preferably from harmful insects, arachnids and nematodes, and even more preferably from insects, acarids and nematodes, wherein insects are most preferred. Preferred insects are Aphids and lepidoptera. Examples for insects are insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata,*

*Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* siphonatera, e.g. *Xenopsylla cheopsis*, Ceratophyllus spp.

Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the microcapsules or the compositions thereof, respectively, are applied on to the plant propagation material by a method such that germination is not induced, e. g. by seed dressing, pelleting, coating and dusting. In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The microcapsules or the aqueous composition can be used as such or in the form of their agrochemical formulations, e. g. in the form of directly sprayable solutions, suspensions, dispersions, emulsions, oil dispersions, by means of spraying, atomizing, dusting, spreading, brushing, immersing or pouring. The application forms depend entirely on the intended purposes; it is intended to ensure in each case the finest possible distribution of the pesticides. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of active substances (also called pesticide) applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e. g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the aqueous compositions, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®.

The present invention has various advantages: The invention reduces the crystallization of the active ingredients; it increases the stability of the formulation within broad range of temperatures; there is a knock-down as well as a residual efficacy; it improves compatibility with other pesticides; it reduces the wind drift; the encapsulated active ingredients are effectively protected from UV-light; the capsules may be loaded with both oil and water soluble active ingredients and adjuvants; the capsules have a increased rainfastness; there is a reduced toxicological effect for the worker and users.

The examples below give further illustration of the invention, which is not, however, restricted to these examples.

EXAMPLES

Solvesso® 200 ND: Aromatic hydrocarbon solvent, distillation range 235-290° C., freezing point −16° C., naphthalene content below 0.9 wt % (commercially available from Exxon).

Solvesso® 150 ND: Aromatic hydrocarbon solvent, distillation range 183-194° C., naphthalene content below 1.0 wt % (commercially available from Exxon).

PVA: Partially hydrolyzed polyvinyl alcohol, viscosity 17-19 mPas (DIN 53015).

PETIA: technical mixture of the tri- and tetraacrylate of pentaerythrite

Example 1

Preparation of Capsules

Water Phase:
  176 g Water
  116 g 10 wt % aqueous solution of polyvinylalkohol PVA
  2 g 2.5 wt % aqueous sodium nitrite solution
Oil Phase
  91 g alpha-cypermethrin
  122 g Solvesso® 200 ND
  61 g Cyclohexanone
  6.4 g Methyl methacrylate
  6.4 g Pentaerythrit tetraacrylate PETIA
  3 g Methacrylic acid
  10 g 2-Benzoyl-5-octyloxyphenol
  Feed 1: 2 g 75 wt % solution of t-butylperpivalat in hydrocarbons
  Feed 2: 3 g 10 wt % solution of t-butylhydroperoxid
  Feed 3: 0.2 g ascorbic acid in 18 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 46.5%. The average particle size D[4,3] was 2.1 µm.

Example 2

Preparation of Capsules

Water Phase:
  133 g Water
  88 g 10 wt % aqueous solution of polyvinylalkohol PVA
  1.5 g 2.5 wt % aqueous sodium nitrite solution
Oil Phase:
  69 g alpha-cypermethrin
  92 g Solvesso® 200 ND
  46 g Cyclohexanone
  4.8 g Methyl methacrylate
  4.8 g Pentaerythrit tetraacrylate PETIA
  2.4 g Methacrylic acid
  17 g 2-Benzoyl-5-octyloxyphenol
  Feed 1: 1.5 g 75 wt % solution of t-butylperpivalat in hydrocarbons
  Feed 2: 2.4 g 10 wt % aqueous solution of t-butylhydroperoxid
  Feed 3: 0.2 g ascorbic acid in 14 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 48.2%. The average particle size D[4,3] was 2.5 µm.

Example 3

Preparation of Capsules

Water Phase:
  124 g Water
  82 g 10 wt % aqueous solution of polyvinylalkohol PVA
  1.4 g 2.5 wt % aqueous sodium nitrite solution
Oil Phase:
  65 g alpha-cypermethrin
  86 g Solvesso® 150 ND
  43 g Acetophenone
  4.5 g Methyl methacrylate
  4.5 g Pentaerythrit tetraacrylate PETIA
  2.3 g Methacrylic acid
  16 g 2-Benzoyl-5-octyloxyphenol
  Feed 1: 1.4 g 75 wt % solution of t-butylperpivalat in hydrocarbons
  Feed 2: 2.3 g 10 wt % aqueous solution of t-butylhydroperoxid
  Feed 3: 0.1 g ascorbic acid in 13 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 20%. The average particle size D[4,3] was 4.9 µm.

Example 4

Preparation of Capsules

Water Phase:
  137 g Water
  132 g 10 wt % aqueous solution of polyvinylalkohol PVA
  2.3 g 2.5 wt % aqueous sodium nitrite solution
Oil Phase:
  94 g alpha-cypermethrin
  126 g Solvesso® 200 ND
  63 g Cyclohexanone
  19 g Methyl methacrylate 19 g Pentaerythrit tetraacrylate PETIA
9.4 g Methacrylic acid
Feed 1: 2.2 g 75 wt % solution of t-butylperpivalat in hydrocarbons
Feed 2: 3.6 g 10 wt % aqueous solution of t-butylhydroperoxid
Feed 3: 0.2 g ascorbic acid in 21 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minuntes and feed 2 and 3 were added in 60 min while the temperature was at 85° C. After cooling to room temperature a suspension of capsules was obtained with a solid content of 52.8%. The average particle size D[4,3] was 1.9 µm.

Example 5

Preparation of Capsules

Water Phase:
  200 g Water
  132 g 10 wt % aqueous solution of polyvinylalkohol PVA
  2.3 g 2.5 wt % aqueous sodium nitrite solution
Oil Phase:
  104 g alpha-cypermethrin
  139 g Solvesso® 200 ND
  69 g 2-Heptanone
  7.3 g Methyl methacrylate
  7.3 g Pentaerythrit tetraacrylate PETIA
  3.6 g Methacrylic acid
  Feed 1: 2.2 g 75 wt % solution of t-butylperpivalat in hydrocarbons
  Feed 2: 3.6 g 10 wt % aqueous solution of t-butylhydroperoxid
  Feed 3: 0.2 g ascorbic acid in 21 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 48.7%. The average particle size D[4,3] was 2.3 µm.

Example 6

Preparation of Capsules

Water Phase:
  133 g Water
  88 g 10 wt % aqueous solution of polyvinylalkohol PVA
  1.5 g 2.5 wt % aqueous sodium nitrite solution
Oil Phase:
  69 g alpha-cypermethrin
  92 g Solvesso® 200 ND
  46 g Cyclohexanone
  7.3 g Methyl methacrylate
  4.8 g Methacrylic acid
  Feed 1: 1.5 g 75 wt % solution of t-butylperpivalat in hydrocarbons
  Feed 2: 2.4 g 10 wt % aqueous solution of t-butylhydroperoxid
  Feed 3: 0.1 g ascorbic acid in 14 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 46.3%. The average particle size D[4,3] was 2.3 µm.

Example 7

Preparation of Capsules

Water Phase:
  139 g Water
  92 g 10 wt % aqueous solution of polyvinylalkohol PVA
  1.6 g 2.5 wt % aqueous sodium nitrite solution
Oil Phase:
  72 g alpha-cypermethrin
  97 g Solvesso® 200 ND
  48 g 2-Heptanone
  5 g Methyl methacrylate
  5 g Pentaerythrit tetraacrylate PETIA
  2.5 g Methacrylic acid
  8 g 2-Benzoyl-5-octyloxyphenol
  Feed 1: 1.5 g 75 wt % solution of t-butylperpivalat in hydrocarbons
  Feed 2: 2.5 g 10 wt % aqueous solution of t-butylhydroperoxid
  Feed 3: 0.1 g ascorbic acid in 14 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 49.4%. The average particle size D[4,3] was 4.3 µm.

Example 8

Preparation of Capsules

Water Phase:
  210 g Water
  120 g 10 wt % aqueous solution of polyvinylalkohol PVA
  2.4 g 2.5 wt % aqueous sodium nitrite solution
Oil Phase:
  94 g alpha-cypermethrin
  126 g Solvesso® 200 ND
  63 g 2-Heptanone
  6.6 g Methyl methacrylate
  6.6 g Pentaerythrit tetraacrylate PETIA
  3.3 g Methacrylic acid
  30 g 2-Hydroxy-4-octyloxybenzophenone
  Feed 1: 2 g 75 wt % solution of t-butylperpivalat in hydrocarbons
  Feed 2: 3.3 g 10 wt % aqueous solution of t-butylhydroperoxid
  Feed 3: 0.2 g ascorbic acid in 19 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 49.2%. The average particle size D[4,3] was 2.5 µm.

Example 9

Preparation of Capsules

Water Phase:
  182 g Water
  120 g 10 wt % aqueous solution of polyvinylalkohol PVA
  2.1 g 2.5 wt % aqueous sodium nitrite solution
Oil Phase:
  97 g alpha-cypermethrin
  130 g Solvesso® 200 ND
  65 g 2-Heptanone
  3.3 g Methyl methacrylate
  3.3 g Pentaerythrit tetraacrylate PETIA
  1.7 g Methacrylic acid
  11 g 2-Benzoyl-5-octyloxyphenol
  Feed 1: 2 g 75 wt % solution of t-butylperpivalat in hydrocarbons
  Feed 2: 3.3 g 10 wt % aqueous solution of t-butylhydroperoxid
  Feed 3: 0.2 g ascorbic acid in 19 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 48.5%. The average particle size D[4,3] was 2.4 µm.

Example 10

Preparation of Capsules

Water Phase:
  553 g Water
  391 g 10 wt % aqueous solution of polyvinylalkohol PVA
  6.8 g 2.5 wt % aqueous sodium nitrite solution
Oil Phase:
  309 g alpha-cypermethrin
  414 g Solvesso® 200 ND
  206 g 2-Heptanone
  16 g Methyl methacrylate
  16 g Pentaerythrit tetraacrylate PETIA
  8 g Methacrylic acid
  Feed 1: 6.5 g 75 wt % solution of t-butylperpivalat in hydrocarbons
  Feed 2: 11 g 10 wt % aqueous solution of t-butylhydroperoxid
  Feed 3: 0.6 g ascorbic acid in 61 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 49.1%. The average particle size D[4,3] was 2.4 µm.

Example 11

Preparation of Capsules

Water Phase:
  213 g Water
  59 g 10 wt % aqueous solution of polyvinylalkohol PVA
  2 g 2.5 wt % aqueous sodium nitrite solution
Oil Phase:
  93 g alpha-cypermethrin
  124 g Solvesso® 200 ND
  62 g 2-Heptanone
  4.8 g Methyl methacrylate
  4.8 g Pentaerythrit tetraacrylate PETIA
  2.4 g Methacrylic acid
  Feed 1: 2 g 75 wt % solution of t-butylperpivalat in hydrocarbons
  Feed 2: 3.2 g 10 wt % aqueous solution of t-butylhydroperoxid
  Feed 3: 0.2 g ascorbic acid in 18 g water The oil phase was added to the water phase at 40° C. while dispersing with a dissolver stirrer at 3500 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 49.2%. The average particle size D[4,3] was 4.2 µm.

Example 12

Preparation of Capsules

Water Phase:
  214 g Water
  220 g 10 wt % aqueous solution of polyvinylalkohol PVA
  4.4 g 2.5 wt % aqueous sodium nitrite solution
Oil Phase:
  160 g alpha-cypermethrin
  246 g Solvesso® 200 ND
  123 g 2-Heptanone
  8.8 g Methyl methacrylate
  838 g Pentaerythrit tetraacrylate PETIA
  4.4 g Methacrylic acid
  Feed 1: 3.7 g 75 wt % solution of t-butylperpivalat in hydrocarbons
  Feed 2: 6 g 10 wt % aqueous solution of t-butylhydroperoxid
  Feed 3: 0.3 g ascorbic acid in 30 g water The oil phase was added to the water phase at 40° C. while dispersing with a dissolver stirrer at 4000 rpm for 15 minutes. Feed 1 was added and the emulsion was heated while stirring in 60 min to 60° C., and in additional 2 h to 70° C. It was heated to 85° C. in 30 minutes and feed 2 and 3 were added in 60 min while the temperature was at 85° C. After cooling to room temperature a suspension of capsules was obtained with a solid content of 54.5%. The average particle size D[4,3] was 2.4 µm.

Examples 13 to 27

Preparation of Capsules

The following examples were prepared according to the previous examples as lined out in the following Table 1.

TABLE 1

Details for examples 14-27.

| Example | Based on Example | Differences | Solid content | Particle size D[4,3] |
|---|---|---|---|---|
| 13 | 2 | 23 g UV absorber instead of 17 g | 51.0% | 3.3 µm |
| 14 | 1 | Solvesso ® 150 ND instead of Solvesso 200 ND and acetophenone instead of cyclohexanone | 48.8% | 2.5 µm |
| 15 | 4 | 2-Heptanone instead of cyclohexanone | 52.9% | 2.3 µm |
| 16 | 4 | Acetophenone instead of cyclohexanone and Solvesso ® 150 ND instead of 200 ND | 53.4% | 2.3 µm |
| 17 | 6 | 6 g MMA instead of 7.3 g; 3.6 g MAA instead of 4.8 g; additional 2.4 g of PETIA | 46.6% | 2.2 µm |
| 18 | 6 | 2.4 g MAA instead of 4.8 g and additional 2.4 g of n-Butylacrylat | 44.2% | 2.4 µm |
| 19 | 7 | 18 g UV absorber instead of 8 g | 51.1% | 2.3 µm |
| 20 | 9 | Cyclohexanone instead of 2-Heptanone | 47.5% | 2.0 µm |
| 21 | 9 | Acetophenone instead of 2-Heptanone | 48.9% | 3.0 µm |
| 22 | 12 | 324 g water instead of 214 g and 110 g PVA instead of 220 g | 53.4% | 2.6 µm |
| 23 | 12 | 253 g water instead of 214 g; 110 g PVA instead of 220 g; 149 g alpha-cypermethrin instead of 160 g; 252 g Solvesso 200 ND instead of 246 g; 126 g 2-Heptanon instead of 123 g | 58.1% | 2.7 µm |
| 24 | 12 | 196 g water instead of 214 g and 158 g alpha-cypermethrin instead of 160 g and 185 g Solvesso 200 ND instead of 246 g and 184 g 2-Heptanon instead of 123 g | 54.9% | 2.3 µm |
| 25 | 12 | 220 g water instead of 214 g and 110 g PVA instead of 220 g and 144 g alpha-cypermethrin instead of 160 g and 240 g Solvesso 200 ND instead of 246 g and 144 g 2-Heptanon instead of 123 g | 59.6% | 2.5 µm |
| 26 | 25 | 192 g Solvesso 200 ND instead of 240 g and 192 g 2-Heptanon instead of 144 g | 58% | 2.6 µm |

Example 27

Preparation of Agrochemical CS Formulation

The capsules raw suspension of examples 1 to 26 was mixed with water and additives while stirring at room temperature. Thus, an aqueous CS agrochemical formulation was obtained containing 10 wt % encapsulated alphacypermethrin, 0.1 wt % antifoam, 0.2 wt % preservative, 10.0 wt % propylene glycol antifreeze, 16 wt % nonionic alkylalkoxylates surfactants, 0.1 wt % xanthan gum and water up to 100%.

Example 28

Preparation of Agrochemical ZC Formulation

A suspension concentrate (SC) was prepared containing 10 wt % suspended alphacypermethrin, 0.1 wt % antifoam, 0.2 wt % preservative, 15 wt % propylene glycol antifreeze, 0.5 wt % xanthan gum, 0.5 wt % dispersant, 0.1 wt % acidic stabilizer and water up to 100%. The resulting SC was mixed with the CS formulation of example 27 while stirring. Thus, an aqueous ZC agrochemical formulation was obtained containing 5 wt % encapsulated alphacypermethrin, 5 wt % suspended alphacypermethrin, 0.1 wt % antifoam, 0.2 wt % preservative, 12.5 wt % propylene glycol antifreeze, 8 wt % nonionic alkylalkoxylates surfactants, 0.3 wt % xanthan gum, 0.2 wt % dispersant, 0.05 wt % acidic stabilizer and water up to 100%.

Example 29

Storage Stability

Samples of the capsule formulation of example 27 (based on examples 1, 7 and 19) were used for storage tests. Samples of all formulations were stored for two weeks either at −10° C. or at +54° C. There was no sediment observable by visual inspection after two weeks.

Example 30

Dispersability

Samples of the capsule formulation of example 27 were used for dispersability tests. The formulations were mixed with standardized water (19.2° dH) into a cylinder shaped graduated glass resulting in a concentration of 0.1 wt % alphacypermethrin (typical application concentration). The spontaneous dispersion were qualitative assessed and after 2 hours the sediment were quantify. All samples were self-dispersing and showed no sediment after 2 hours.

Example 31

UV Stability

Duplicate samples were irridated with light (300-800 nanometer, 650 $W/m^2$) for 46 h at room temperature. The concentration of alphacypermethrin in the sample was analyzed by HPLC before and after the UV exposure in order to calculate the recovery after irridation (Table 2). Fastac® EC is an emulsion concentrate of alphacypermethrin (100 g/l in solvent naphta) and is commercially available from BASF SE.

TABLE 2

Results of light stability testing

| Sample | Recovery without irridation [%] | Recovery after irridation [%] |
|---|---|---|
| Example 5 | 102.6 | 50.2 |
|  | 99.0 | 46.5 |
| Example 7 | 92.0 | 51.7 |
|  | 92.1 | 54.2 |
| Example 19 | 92.2 | 61.5 |
|  | 91.8 | 58.2 |
| Example 13 | 92.2 | 52.5 |
|  | 89.5 | 55.0 |
| Fastac ® EC[a)] | 111.2 | 13.7 |
|  | 97.5 | 13.6 |

[a)]comparative, not according to the invention

We claim:

1. A stable aqueous composition comprising
   a suspended pesticide A, and
   microcapsules comprising a shell and a core, wherein
   (a) the core contains a pesticide B, 2-heptanone, and a water-immiscible solvent A;
   (b) the shell contains poly(meth)acrylate, which comprises monomers selected from the group consisting of $C_1$-$C_4$ alkyl esters of acrylic acid, $C_1$-$C_4$ alkyl esters of methacrylic acid, acrylic acid, methacrylic acid, maleic acid, pentaerythritol tri tetraacrylate, and mixtures thereof, in polymerized form;
   wherein solvent A is a hydrocarbon, a vegetable oil, a fatty acid ester, methyl or ethyl-ester of a vegetable oil, or mixtures thereof;
   wherein the weight ratio of solvent A to 2-heptanone is 3:1 to 1:2; wherein the water-solubility of pesticide B is less than 10 g/l at 20° C.; and wherein the solubility in water of solvent A is up to 50 g/L at 20° C.

2. The composition according to claim 1, wherein the pesticide B is present in dissolved form.

3. The composition according to claim 1, wherein the pesticide A has a solubility in water of less than 10 g/l at 20° C.

4. The composition according to claim 1, wherein solvent A is a hydrocarbon.

5. The composition according to claim 1, wherein the weight ratio of the sum of all pesticides in the core to the sum of all solvents in the core is from 1:1 to 1:10.

6. The composition according to claim 1, wherein the microcapsule contains up to 7 wt % poly(meth)acrylate, based on the total amount of all pesticides in the core, all solvents in the core, and the poly(meth)acrylate.

7. A method for preparing the composition as defined in claim 1, comprising mixing the pesticide A, water and the microcapsules.

8. A method for controlling phytopathogenic fungi and/or undesired plant growth and/or undesired attack by insects or mites and/or for regulating the growth of plants, where the aqueous composition as defined in claim 1 is applied to the particular pests, their habitat or the plants to be protected from the particular pest, the soil and/or on undesired plants and/or the useful plants and/or their habitat.

9. The method of claim 8, wherein the pesticide B is present in dissolved form.

10. The method of claim 8, wherein the pesticide A has a solubility in water of less than 10 g/l at 20° C.

11. The method of claim 8, wherein solvent A is a hydrocarbon.

12. A microcapsule comprising a shell and a core, wherein
   (a) the core contains a pesticide B, 2-heptanone, and a water-immiscible solvent A;
   (b) the shell contains poly(meth)acrylate, which comprises monomers selected from the group consisting of $C_1$-$C_4$ alkyl esters of acrylic acid, $C_1$-$C_4$ alkyl esters of methacrylic acid, acrylic acid, methacrylic acid, maleic acid, pentaerythritol tri- and tetraacrylate, and mixtures thereof, in polymerized form;
   wherein solvent A is a hydrocarbon, a vegetable oil, a fatty acid ester, methyl or ethyl-ester of a vegetable oil, or mixtures thereof;
   wherein the weight ratio of solvent A to 2-heptanone is 3:1 to 1:2; wherein the water-solubility of pesticide B is less than 10 g/l at 20° C.; wherein the solubility in water of solvent A is up to 50 g/l at 20° C.; wherein the weight ratio of the pesticide B to the sum of all solvents in the core is from 1:1 to 1:10, and wherein the microcapsule contains up to 7 wt % poly(meth)acrylate, based on the total amount of all pesticides in the core, all solvents in the core, and the poly(meth)acrylate.

13. A method for preparing the microcapsules as defined in claim 12, comprising heating an oil-in-water emulsion, which contains a radical initiator, the solvent A, 2-heptanone, the pesticide B, and a monomer selected from $C_1$-$C_4$ alkyl esters of acrylic acid, $C_1$-$C_4$ alkyl esters of methacrylic acid, acrylic acid, methacrylic acid, maleic acid, PETIA, and mixtures thereof, and obtaining the microcapsules.

* * * * *